United States Patent
Willing et al.

(10) Patent No.: US 8,330,107 B2
(45) Date of Patent: Dec. 11, 2012

(54) GAS SENSOR AND PROCESS FOR MEASURING MOISTURE AND CARBON DIOXIDE CONCENTRATION

(75) Inventors: Bert Willing, Blonay (CH); Markus Kohli, Grandson (CH); Andreas Seifert, Denens (CH)

(73) Assignee: Axetris AG, Kagiswil (CH)

( * ) Notice: Subject to any disclaimer, the term of this patent is extended or adjusted under 35 U.S.C. 154(b) by 218 days.

(21) Appl. No.: 12/861,942

(22) Filed: Aug. 24, 2010

(65) Prior Publication Data

US 2011/0304844 A1 Dec. 15, 2011

(30) Foreign Application Priority Data

Jun. 15, 2010 (EP) .................................... 10006204

(51) Int. Cl.
*G01J 1/00* (2006.01)
(52) U.S. Cl. .................................................. 250/336.1
(58) Field of Classification Search ...... 250/336.1–336.2
See application file for complete search history.

(56) References Cited

U.S. PATENT DOCUMENTS

2007/0069131 A1* 3/2007 Banerjee et al. ........... 250/339.1

FOREIGN PATENT DOCUMENTS

DE 102 20 668 A1 11/2003

OTHER PUBLICATIONS

Kormann et al., "Application of a multi-laser tunable diode laser absorption spectrometer for atmospheric trace gas measurements at sub-ppbv levels," 2002, SpectroChimica Acta Part A vol. 58, pp. 2489-2498.*
Lucchesini et al., "Diode laser spectroscopy of CO2 at 790 nm," 2007, Journal of Quantitative Spectroscopy & Radiative Transfer, vol. 103, pp. 74-82.*

* cited by examiner

*Primary Examiner* — Kiho Kim
(74) *Attorney, Agent, or Firm* — Renner, Otto, Boiselle & Sklar, LLP

(57) ABSTRACT

An TDLS gas sensor with a measuring pick-up to be arranged outside of the interior chamber of an incubator or a climate chamber of similar design, and with an absorption pick-up to be arranged inside the interior chamber, and also with a window separating the measuring area and absorption area for the atmospheric separation of the laser diode from the interior chamber of the incubator, with the window being arranged at an angle to the axis of the laser beam emitted by a laser diode, and with the optronic components being arranged in a block of material in the measuring pick-up, said block being made of thermally well-conducting material and serving as heat sink, and with a heating system for the window in the measuring pick-up. In addition, a process for measuring the moisture and the carbon dioxide concentration.

15 Claims, 2 Drawing Sheets

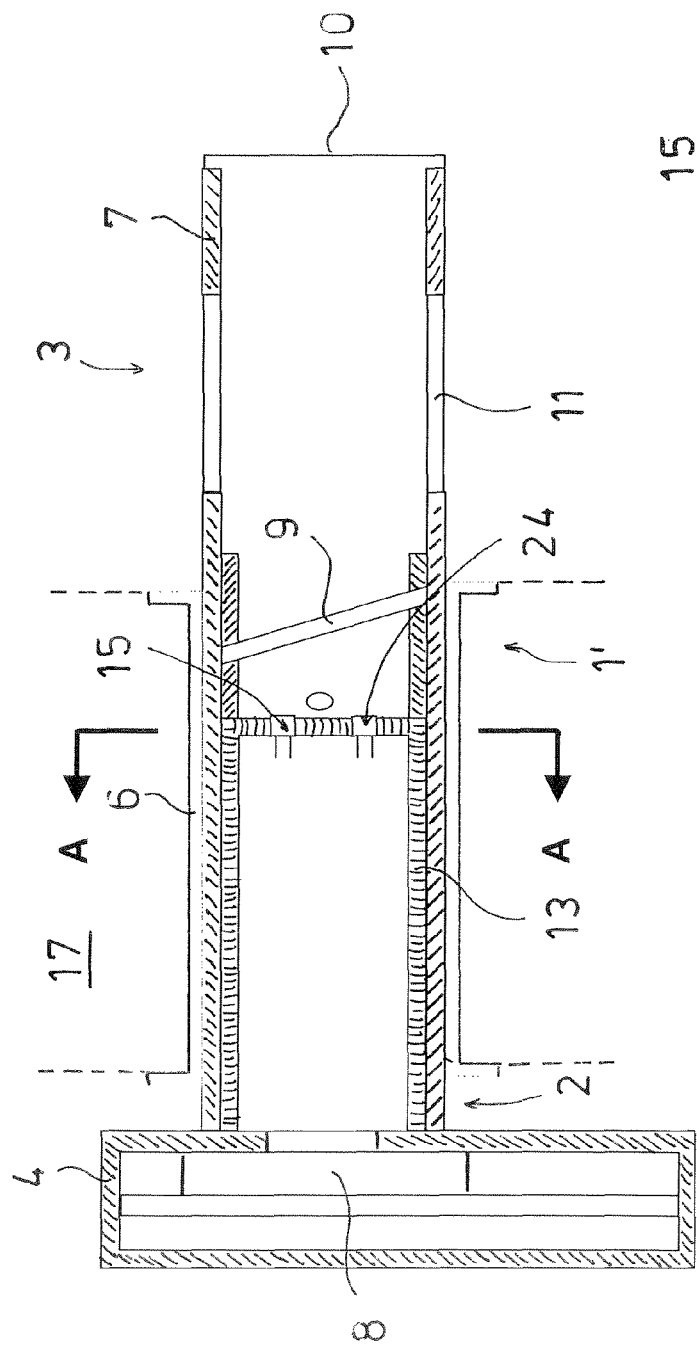
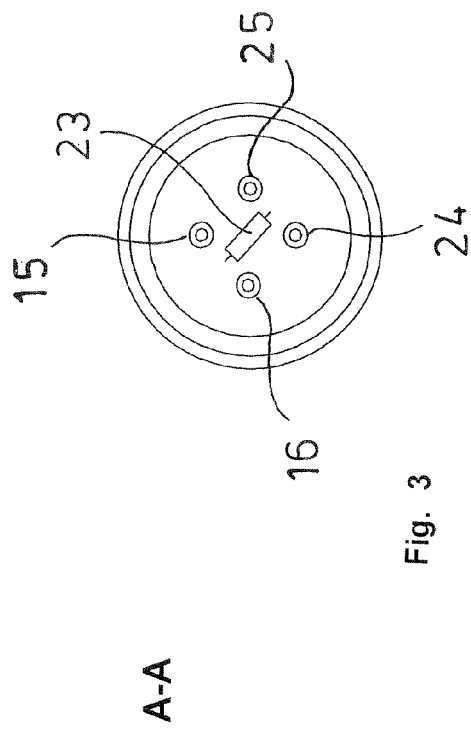
Fig. 2
Fig. 3

GAS SENSOR AND PROCESS FOR MEASURING MOISTURE AND CARBON DIOXIDE CONCENTRATION

CROSS-REFERENCE TO RELATED APPLICATION

The present application claims priority under 35 USC §119 to European Patent Application No. 10 006 204.1 filed Jun. 15, 2010, the entire disclosure of which is incorporated herein by reference.

TECHNICAL FIELD OF THE INVENTION

This invention relates to a TDLS (Tunable Diode Laser Spectrometry) gas sensor for at least the measuring of carbon dioxide ($CO_2$) and a process for at least the measuring of moisture ($H_2O$) and of carbon dioxide ($CO_2$) in an incubator or in climate chambers of similar design. Specifically, the invention relates to a TDLS gas sensor with a measuring pick-up with optronic components that comprises at least one laser diode as emitter and a detector for the laser beam emitted by the laser diode, and with an absorption pick-up that has a volume in which the gas to be measured can circulate from an interior chamber of the incubator and in which the laser beam propagates, and with at least one reflector that guides the laser light emitted by the laser diode to the detector.

DESCRIPTION OF THE RELATED ART

A gas sensor of this type is known from DE 102 20 668 A1.

The TDLS measuring principle is commonly known and represents a highly selective and versatile technology for measuring many traces of atmospheric substances with a detection sensitivity in the ppb range. Here, the concentration of the gas or of the gas component to be examined is determined from a measured absorption. A laser diode is used as a radiation source.

For biological applications, cell phylae, among others, are grown in so-called cell incubators. A defined atmosphere ($CO_2$ content, oxygen content, moisture) and a defined temperature are maintained in the interior of the incubator, and the relevant parameters are controlled by means of sensors. After removal of the cell cultures, it is common to first sterilize the incubator before the next operating cycle. This is done either at a relative humidity of 100% and a temperature of 90° C., or in an increasing fashion at a relative humidity of well below 100% and a temperature of up to 200° C., each for several hours. However, current $CO_2$ sensors as well as moisture sensors are constructed so that they do not survive a temperature of 200° C., even when they are switched off because they are located in the interior chamber of the incubator and because the relevant electronic components for signal processing have a maximum storage temperature that is significantly lower. For this reason, it is necessary to remove the sensors prior to such a sterilization which, on the one hand, means extra work for personnel not familiar with sensor systems, and, on the other hand, leaves the sensors in an undefined state of sterilization. As $CO_2$ sensors, either very inaccurate thermal conductivity sensors are used, or NDIR (Non Diffractive Infrared) sensors whose installation inside the incubator is essential due to their construction.

The principal difficulties of a sensor for measurements in an incubator or in a climate chamber of similar design arise from the temperature profile prevailing in the gas sensor because the incubator is operated at 37° C. and is sterilized at higher temperatures of up to 200° C. while laser and photo diodes must not become hotter than approximately 80° C. Another problem for measurement are back-reflections into the laser diode that may cause an unstable condition.

SUMMARY OF THE INVENTION

This invention therefore addresses the problem by proposing a possibility that, under a wide variety of environmental influences, permits an accurate measurement of at least $CO_2$ that is undisturbed by reflections and may remain in installed condition even during sterilization. This invention also addresses the problem of proposing a process for the simultaneous measurement of carbon dioxide and moisture.

According to the invention, this problem is solved by a TDLS gas sensor and a process with the characteristics of the independent related claims. Additional advantageous embodiments are given in the related dependent claims.

According to the invention, a gas sensor of the type characterized above and based on the TDLS measuring principle is used that has a window for separating the laser diode from the interior chamber and therefore from the atmosphere of the incubator, with the window arranged at an angle to the axis of the laser beam emitted by the laser diode. In addition, the TDLS gas sensor comprises a block of material made of thermally well-conducting material serving as heat sink that is located in the measuring pick-up and accepts the optronic components, specifically the laser diode and the detector, and has a heating system for the window in the measuring pick-up.

The measuring pick-up and absorption pick-up unit forming the TDLS gas sensor may be assembled either before its installation into the opening in the wall of the incubator or after the measuring pick-up has been inserted into the wall of the incubator. Any wall of the incubator may be chosen for this purpose, for example a side wall, a bottom, or a lid. Among other things, these different implementations depend on whether the laser is operated with a diverging beam so that, with regard to the required absorption path, the diameter of the mirror for back-reflection and back-focusing is too large for an insertion into the incubator from the outside. In this case, the measuring pick-up can be inserted into an opening in the wall of the incubator and can be connected with the absorption pick-up inside the interior chamber of the incubator for the optical alignment of laser diode, reflector, and detector. When a collimated laser beam is used, and with the diameter significantly smaller, the complete TDLS gas sensor can be inserted into the wall of the incubator from the outside. The design of the TDLS gas sensor according to the invention permits a functionally reliable and accurate measurement. The window that is arranged at an angle to the axis of the laser diode and which may be made of a crystalline or amorphous glass material that is permeable for the laser beam, or of some other suitable solid body, prevents back-reflections that might have a negative influence on the measurement. In addition, the window serves to separate the different atmospheres because the laser diode and photo diode must not become hotter than 60 to 65° C. A wedge window may also be used as window. In order to ensure the heat dissipation in the incubator at higher temperatures, the optronic components like laser diode and photo diode are located in a block of material made of thermally well-conducting material, preferably in a block of aluminum, for example, that serves as a heat sink towards the ambient temperature. In addition, a heating system for the window ensures that no condensation forms on the window during normal operation. Without a heating system, condensation forms because, with normal operation of the incubator at a relative humidity of almost 100% in the interior chamber of the incubator and heat dissipation through the window and the block of material, the window has a lower temperature than the interior chamber of the incubator. The heating system may consist of a coating, an infrared radiator, a ballast resistor, or similar suitable devices that ensure that, during normal operation of the incubator, the heat generated by the heating system prevents condensation from forming on the window. This heating system is switched off during sterilization operations.

According to a preferred embodiment of the TDLS sensor, the electronic control and analysis system also measures by means of the laser diode the moisture at a wavelength in a range from 1950 to 1960 nm, preferably 1953 nm. Accordingly, it is possible to measure with the TDLS gas sensor $CO_2$ as well as $H_2O$ with one device and in one measuring cycle, for example 10 seconds $CO_2$ and 10 seconds moisture, because the wavelength of the associated absorption lines are within the tuning range of the diode laser. For this purpose, the measuring cycle may consist of a single pass through the entire tuning range, or of alternating passes through two range sections that correspond to the absorption wavelengths of $CO_2$ and $H_2O$. The two measurements may consist of parallel or serial measurements.

Advantageously, the adjacent $CO_2$ and $H_2O$ absorption lines are measured at 1953 nm by means of the electronic control and analysis system, thereby compensating for the cross sensitivity between $CO_2$ and $H_2O$.

Regarding their design, the measuring pick-up and the absorption pick-up may be rectangular- or cylindrical-shaped on the outside. It is essential that the optical alignment of the elements required for the measurement, such as the laser diode, the reflector, and the detector, is suitable for the measurement and does not change during assembly. The window should let the laser beams pass without hindrance, and will therefore consist preferably of glass with the highest possible resistance against glass erosion. In principle, the window may be arranged on the measuring pick-up or on the absorption pick-up. The beam enters the incubator through the window, with the reflector arranged so that it is located at a selectable distance from the wall of the incubator. Through the openings in the walls of the absorption pick-up and/or the reflector, the gas to be examined passes into the space between the reflector and the window. According to an advantageous embodiment, the TDLS gas sensor is designed as a separable measuring pick-up and absorption pick-up unit. The measuring pick-up may be connected with the absorption pick-up arranged in the interior chamber by means of a thread or a bayonet lock. In the area of the absorption pick-up, the TDLS sensor provides a seal relative to the wall of the incubator.

According a preferred embodiment, in the area of the measuring pick-up, the TDLS gas sensor has a tube-shaped section made of a plastic material of high thermal strength with which it can be inserted into the opening in the wall of the incubator. The laser diode and the detector, preferably a photo diode, are arranged at a defined distance in the massive block of material made of thermally well-conducting material, preferably of aluminum. The preferred tube-shaped section is made of a plastic material of high thermal strength, for example PPS, in order to prevent a thermal transfer from the wall of the incubator to the electronic components in order to protect them. The distance of the laser diode is determined by the requirement that, with an operating temperature of the incubator of 200° C. for the sterilization, the temperature of 180° C. at the window must drop to below 65° C. at the laser diode.

In another embodiment of the invention, the tube-shaped section is centered at least in the area of the block of material with the laser diode and the photo diode inside in relation to the absorption pick-up, for example by means of a cone, with a compression spring located on the rear side—i.e. the side opposite the laser diode—of the block of material made of thermally well-conducting material fixing this block in position in the tube-shaped section or also on the absorption pick-up. Preferably, the spring presses a cone located on the block of material into an associated mating surface on the absorption pick-up so that the laser diode and the photo diode in the measuring pick-up and the reflector in the absorption pick-up rest in a clearly defined position relative to each other.

In another embodiment of the invention, the absorption pick-up is shaped as a cylindrical part that comprises the reflector at its one end and, at its other end, a window and circumferential walls with elongated recesses in a tube section that can be inserted into the wall of the incubator. Designing the absorption pick-up as a cylindrical part offers advantages for the manufacturing process. Relative to the measuring pick-up, the absorption pick-up provides a gas-tight seal with a window and holds the reflector at a distance from the wall of the incubator. According to another preferred embodiment of the invention, the reflector consists of a convex mirror, preferably made of electro-chemically polished stainless steel.

Electro-chemically polished stainless steel is preferred because vapor-deposited mirrors age very quickly in very hot and humid atmospheres. The absorption pick-up is made of a plastic material with high thermal strength, for example PPS. According to another embodiment, the photo diode is not positioned at the exact focal point of the convex mirror but slightly in front of or behind it in order to prevent possible adjustment tolerances from causing the beam to shift.

According to the process, the measurement of moisture and carbon dioxide in the interior chamber of an incubator or a climate chamber of similar design is performed, based on the TDLS principle, by means of the sensor equipped according to the invention, by measuring the absolute moisture and the carbon dioxide concentration in one measuring cycle. Here, the laser diode is preferably operated at a wavelength of 1950 to 1960. This is used to measure the adjacent carbon dioxide and water absorption lines at 1953 nm so that the cross sensitivities between carbon dioxide and moisture can be compensated by adjacent carbon dioxide and water absorption lines. Preferably, oxygen is also measured by means of an additional diode in a wavelength range of 760 nm that is suitable for this purpose. Advantageously, the heating system for the window is switched on only during normal operation. The directed radiation of the laser in combination with a wavelength for which regular window glass is permeable therefore permits a measuring setup where the entire electronic components (laser diode, photo diode, electronic control and analysis system) are located outside the incubator and are maintained at room temperature. Due to the design of the sensor, the window arranged in the absorption pick-up is at the same temperature as the interior chamber of the incubator. If it were even at a slightly lower temperature than the temperature of the incubator, the high humidity in the incubator would cause condensation to form on the window, which would have a negative effect on the operation of the sensor. The laser beam is sent through the window into the interior chamber of the incubator, where it is reflected by the mirror, and again passes through the window towards the photo diode. Window, mirror, and mirror holder can be made cost-efficiently from materials that are able to endure the sterilization methods used here over the long term without negative effect. As a consequence, the sensor does not need to be removed during the sterilization cycle and is sterilized at the same time. Due to the fact that the gas sensor consists preferably of two components that are easy to separate, i.e. the measuring pick-up and the absorption pick-up, contaminations (dust, condensation, cell residues droplets of solvents) can easily be removed by cleaning. In addition, the absorption pick-up is a component that can easily be replaced without special knowledge by the end user of the incubator, without the need for expensive components to be replaced at the same time.

Additional characteristics of the invention are given in the following description of the embodiment of the invention in conjunction with the claims of the preceding description and the figures. The individual characteristics may be realized either individually by themselves or in combinations of several in embodiments of the invention.

BRIEF DESCRIPTION OF THE DRAWINGS

FIG. 2 shows the longitudinal section through a TDLS gas sensor shown in a schematic view with an additional laser diode for the oxygen measurement, where the entire TDLS gas sensor can be inserted into an opening in the wall of the incubator, and FIG. 3 shows a cross section along the line A-A through the TDLS gas sensor according to FIG. 2.

DETAILED DESCRIPTION OF THE INVENTION

Figure 1:
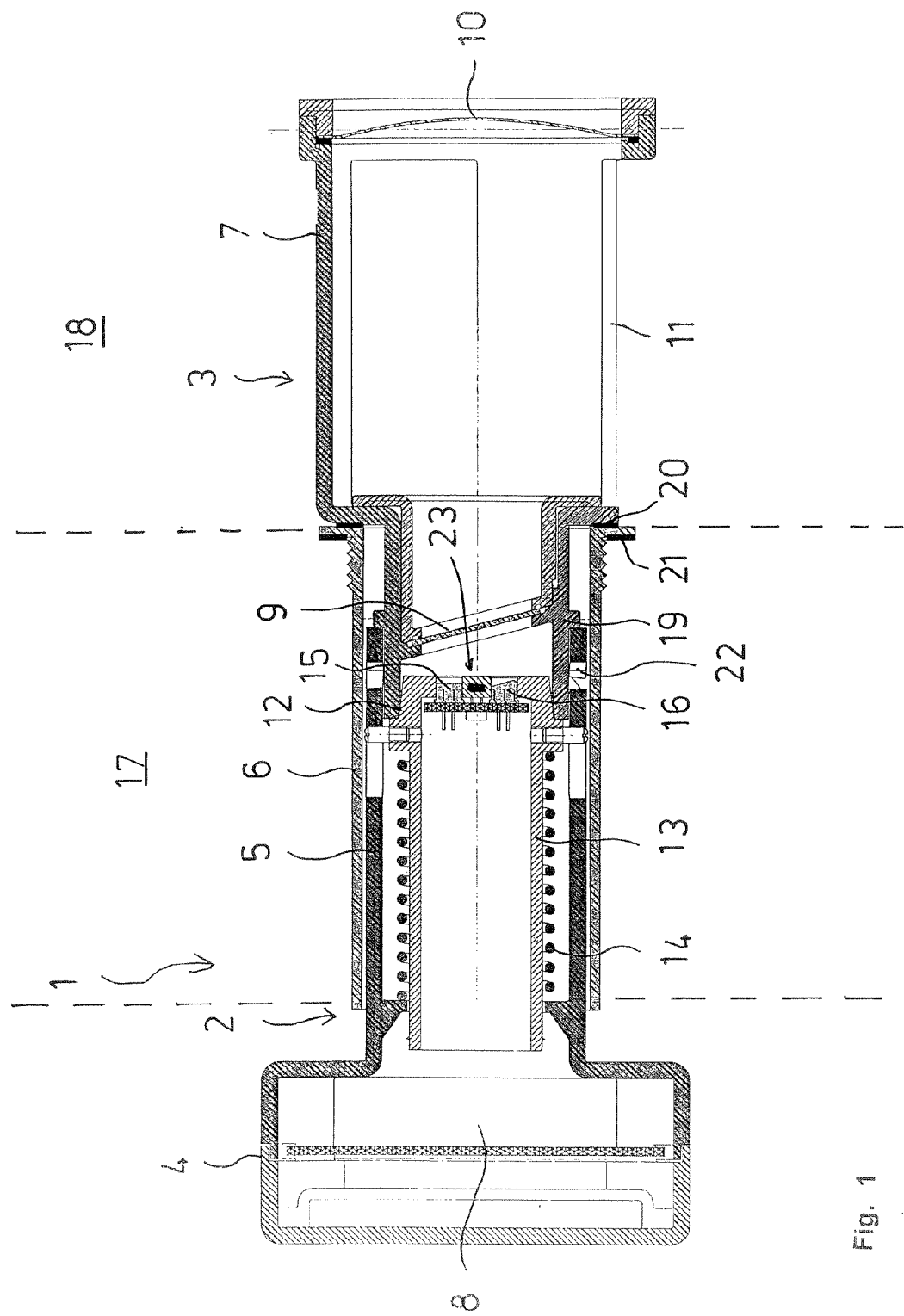
FIG. 1 shows a longitudinal section through a TDLS gas sensor with a measuring pick-up and an absorption pick-up, with the absorption pick-up from the interior chamber of the incubator being connectable with the measuring pick-up that is inserted in an opening of the incubator.

FIG. 1 shows the longitudinal section through the TDLS gas sensor 1 in a tube-shaped wall entrance 6 that is located in a wall (not shown, indicated by 17) of an incubator. The TDLS gas sensor 1 has a measuring pick-up 2 and an absorption pick-up 3. The measuring pick-up 2 is located outside of an interior chamber (not shown, indicated by 18) of the incubator, partially in the wall 17 of the incubator. Depending on the design of the incubator, the wall 17 may consist of double walls with heating systems located in between the walls, or of a single wall with insulation applied on the outside. The measuring pick-up 2 has a box-shaped housing section 4 and an adjacent tube-shaped housing section 5. The electronic control and analysis system 8 is located in the housing section 4. In a cylindrical aluminum block 13, a laser diode 15 and a photo diode 16 are located in the tube-shaped housing section 5. The aluminum block 13 serves as a heat sink. If required, it may be made from a solid piece, and a head with the laser diode 15 and the photo diode 16 may be attached to the end. On its face side accepting the laser diode 15 and the photo diode 16, the aluminum block 13 is shaped conically at its circumference in order to serve as a centering feature 12 for the aluminum block 13 in an adapted tube section 19 of the absorption pick-up 3. By means of a spring 14 that is supported on the housing section 4 in the sample embodiment, the aluminum block 13 is pressed into the tube section 19 with its conical centering feature 12, thereby ensuring the centric position of the laser diode 15 and the photo diode 16.

The absorption pick-up 3 has a cylindrical housing 7 with recesses 11 following the tube section 19 through which the gas to be measured is able to pass. Therefore, with its measuring section, the absorption pick-up 3 is located inside the interior chamber 18 of the incubator, and the tube section 19 located in the wall 17 serves to support it in the wall 17, for fixing in position on the measuring pick-up 2, and for the optical alignment. Sealing relative to the wall 17 of the incubator is accomplished with the seal 20 between the housing 7 and the absorption pick-up 3 and the wall entrance 6, and with a seal 21 between the wall entrance 6 and the wall 17. In the tube section 19, an inclined plane-parallel glass window 9 is located that seals the interior chamber 18 of the incubator against the measuring pick-up 2 so that the function of the laser diode 15 is not impaired. At the end of the absorption pick-up 3 that is opposite the window 9, the housing 7 contains a convex mirror 10 of electro-chemically polished stainless steel. The measuring pick-up 2 is inserted into the wall entrance 6 and is fixed in position with the absorption pick-up 3 from the inside by means of a bayonet lock 22. Expediently, prior to that, the housing section 4 and along with it the measuring pick-up 2 is attached to the wall 17 or in the wall entrance 6 by means of suitable devices, for example by means of bolts, because normally it is not possible for one person to hold the measuring pick-up 2 and the absorption pick-up 3 simultaneously. The centric arrangement ensures that the optical elements remain aligned with each other during assembly.

The aluminum block 13 is positioned at a distance from the window 9 so that the laser diode 15 and the photo diode 16 are not exposed to the high temperature occurring in the incubator during sterilization. The resulting dead space of the entire measuring section from the laser diode 15 to the mirror 10 that is not exposed to the gas to be examined must be taken into account when analyzing the measuring signal. The actual absorption path is the area between the window 9 and the mirror 10. The distance between the window 9 and the laser diode 15 has a value of 8 to 10 mm, and, if necessary, and compared to the representation in the figure, the tube section 19 may be shortened in order to increase the distance. In the sample embodiment, a thermal resistor 23 that provides for the heating of the window 9 during normal operation is located between the photo diode 16 and the laser diode 15.

With a required measuring accuracy of approximately 2000 ppm $CO_2$, the laser diode 15 does not need to be operated in collimated condition. The beam passes through the inclined plane-parallel window 9 into the interior chamber of the incubator and, at a distance of approximately 10 cm, is focused back through the window 9 onto the photo diode 16 by the convex mirror 10 with a diameter of 50 mm, with the photo diode not being positioned exactly at the focal point of the mirror 10 but slightly in front of or behind it. The window 9 is inclined in order to avoid or reduce back-reflections towards the laser diode 15.

In a schematic view, FIG. 2 shows the longitudinal section through a TDLS gas sensor 1' that has a smaller diameter and can therefore be inserted with a tube-shaped housing section 26 through the wall entrance 6 as a complete unit. In this embodiment, an additional laser diode 24 and an additional photo diode 25 are provided to be able to also perform oxygen measurements with this gas sensor. The remaining parts are configured in accordance with the TDLS gas sensor 1 in FIG. 1. Of course, the gas sensor 1 according to FIG. 1 can also be equipped with an additional laser diode for measuring oxygen, or the embodiment according to FIG. 2 may be configured without an additional laser diode 24 and photo diode 25.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. A TDLS gas sensor for measuring carbon dioxide concentration ($CO_2$ concentration) in an incubator or climate chambers of similar design with:
   a measuring pick-up with optronic components that comprises at least one laser diode as emitter and a detector for a laser beam emitted by the laser diode; and
   an absorption pick-up that has a volume in which the gas to be measured can circulate from an interior chamber of the incubator and in which the laser beam propagates, and with at least one reflector that guides the laser light emitted by the laser diode to the detector, and
   wherein the measuring pick-up and the absorption pick-up are separated atmospherically by a window and the optronic components in the measuring pick-up are thermally uncoupled from the absorption pick-up, and
   the window is arranged at an angle to the axis of the laser beam emitted by the laser diode.

2. The TDLS gas sensor as claimed in claim 1, wherein the optronic components in the measuring pick-up are arranged in a block of material made of thermally well-conducting material, preferably in a metal block, that serves as heat sink.

3. The TDLS gas sensor as claimed in claim 2, wherein the block of material with the laser diode and the detector is centered relative to the absorption pick-up, and a spring on the rear side of the block of material opposite the laser diode presses said block into a centering feature.

4. The TDLS gas sensor as claimed in claim 1, comprising a heating system for the window that prevents condensation on the window by heating it.

5. The TDLS gas sensor as claimed in claim 1, wherein the thermal uncoupling between the optronic components and the absorption pick-up is accomplished by means of a mechanical connection from the measuring pick-up to the absorption pick-up comprising a plastic material of high thermal strength.

6. The TDLS gas sensor as claimed in claim 1, wherein an electronic control and analysis system additionally measures the moisture by means of the laser diode at a wavelength in the range from 1950 to 1960 nm, thereby compensating the cross sensitivities between carbon dioxide and moisture.

7. The TDLS gas sensor as claimed in claim 1, wherein the measuring pick-up has an additional laser diode for measuring oxygen ($O_2$) and for its analysis by means of an electronic control and analysis system.

8. The TDLS gas sensor as claimed in claim 1, wherein the measuring pick-up and the absorption pick-up form a separable unit.

9. The TDLS gas sensor as claimed in claim 1, wherein the mechanical connection from the measuring pick-up to the absorption pick-up comprises a tube-shaped section in the area of the measuring pick-up with which it can be inserted into the wall of the incubator, and the laser diode and the detector are arranged in the block of material at a defined distance from the wall.

10. The TDLS gas sensor as claimed in claim 1, wherein the absorption pick-up is shaped as a cylindrical part that has the reflector at one end and on the other end the window and circumferential walls that have recesses.

11. The TDLS gas sensor as claimed in claim 1, wherein the reflector comprises a convex mirror, made of electro-chemically polished stainless steel, and the detector is not located exactly in the focal point of the convex mirror.

12. A process for measurement of moisture and carbon dioxide in the interior chamber of an incubator or a climate chamber of similar design, based on the TDLS principle, with a sensor as claimed in claim 1, wherein the moisture and the carbon dioxide concentration are measured in one measuring cycle.

13. The process as claimed in claim 12, wherein a measurement of oxygen is performed by means of an additional laser diode.

14. The process as claimed in claim 12, wherein the heating system for the window is only switched on during the normal operation of the incubator.

15. The process as claimed in claim 12, wherein during the one measuring cycle the laser diode is operated at a wavelength of 1950 nm to 1960 nm.

\* \* \* \* \*